US010660327B2

(12) United States Patent
Xing

(10) Patent No.: US 10,660,327 B2
(45) Date of Patent: May 26, 2020

(54) MULTILAYER INSULATION OF BIOLOGICAL SAMPLES AND COOLING BY IMMERSING IN A CRYOGENIC LIQUID FOR CRYOPRESERVATION

(71) Applicant: Xiaojun Xing, New Haven, CT (US)

(72) Inventor: Xiaojun Xing, New Haven, CT (US)

(*) Notice: Subject to any disclaimer, the term of this patent is extended or adjusted under 35 U.S.C. 154(b) by 0 days.

(21) Appl. No.: 15/200,206

(22) Filed: Jul. 1, 2016

(65) Prior Publication Data
US 2017/0000109 A1    Jan. 5, 2017

Related U.S. Application Data

(60) Provisional application No. 62/187,815, filed on Jul. 2, 2015.

(51) Int. Cl.
*A01N 1/02* (2006.01)
*G01N 33/487* (2006.01)

(52) U.S. Cl.
CPC .......... *A01N 1/021* (2013.01); *A01N 1/0242* (2013.01); *G01N 33/487* (2013.01)

(58) Field of Classification Search
None
See application file for complete search history.

(56) References Cited

U.S. PATENT DOCUMENTS

| 4,251,995 A | 2/1981 | Pert et al. | |
|---|---|---|---|
| 4,262,494 A * | 4/1981 | Karow, Jr. | A01N 1/02 62/384 |
| 7,604,930 B1 | 10/2009 | Gao et al. | |
| 2008/0026366 A1* | 1/2008 | Harkins | G01N 1/30 435/5 |
| 2013/0091890 A1* | 4/2013 | Schryver | B65D 81/38 62/440 |

FOREIGN PATENT DOCUMENTS

CN    1299636 A    6/2001

OTHER PUBLICATIONS

Arav, A. et al. 2002. New trends in gamete's cryopreservation. Molecular and Cellular Endocrinology 187: 77-81. specif. pp. 77.*
Cryopreservation and Freeze-Drying Protocols. Freezing in Glass Capillaries. Copyright 2007 Human Press, Inc. Second edition. Eds: John G. Day & Glyn N. Stacey. Totowa, NJ. pp. 83-85. specif. pp. 83, 85.*
Isachenko, V. et al. 2004. Cryoprotectant-free cryopreservation of human spermatozoa by vitrification and freezing in vapor: Effect on motility, DNA integrity, and fertilization ability. Biology of Reproduction 71: 1167-1173. specif. p. 1167, 1172, 1173.*
EngMT. Xing. New method of producing frozen bull semen. Chinese Patent Application Publication No. CN1299636(A); Date of Publication: Jun. 20, 2001. pp. 1-7. specif. pp. 1, 3, 4, 5, 6, 7.*
Khuu, H.M. et al. 2002. Catastrophic failures of freezing bags for cellular therapy products: description, cause, and consequences. Cytotherapy 4(6): 539-549. specif. pp. 539, 548.*
Nakagata, Naomi; Cryopreservation of Mouse Spermatoza and in Vitro Fertilization; Transgenic Mouse Methods and Protocols, Methods in Moelcular Biology, vol. 693, pp. 57-72, 2011.
Imv Technologies; Digitcool Programmable Automatic Freezers; 6 pages, 2011.
Curry, Mark R.; Cryopreservation of Semen From Livestock; 2000 Journals of Reproduction and Fertility 1359-6004/2000, pp. 46-52.
Disanto, Marlea; Tarozzi, Nicoletta; Nadalini, Marco; Borini, Andrea; Human Sperm Cryopreservation:Update on Techniques, Effect on DNA Integrity, and Implications for Art; Hindawi Publishing Corporation, Advances in Urology, vol. 2012, Article ID 854837, 12 pages, 2012.
Alvarenga, Marco Antonio; Papa, Frederico Ozanam; Neto, Carlos Ramires; Advances in Stallion Semen Cryopreservation; Department of Animal Reproduction and Veterinary Radiology, Sao Paulo State University—UNESP, Botucatu, Brazil, pp. 521-530, 2016.
Sieme, Harald and Oldenhof, Hariette; Cryopreservation of Semen From Domestic Livestock; Cryopreservation and Freeze-Drying Protocols, Methods in Molecular Biology, vol. 1257, pp. 277-287, 2015.
Moce, Eva; Fajardo, Andres J.; Graham, James K.; Human Sperm Cryopreservation; European Medical Journal, Jan. 2016, pp. 86-91.
Walters, Eric M.; Benson, James D.; Woods, Erik J.; Critser, John K.; The History of Sperm Cryopreservation; Cambridge University Press 2009, pp. 1-10.
Tiersch, Terrence R., Yang, Huipang E. Hu; Outlook for Development of High-Throughput Cryopreservation for Small-Bodied Biomedical Model Fishes; Comparative Biochemistry and Physiology, Part C 155 (2012) pp. 49-54.

(Continued)

*Primary Examiner* — Renee Claytor
*Assistant Examiner* — Sharon M. Papciak
(74) *Attorney, Agent, or Firm* — DeLio Peterson & Curcio LLC; Peter W. Peterson

(57) ABSTRACT

A container system and method for cryopreservation of sperm includes first containers having walls of a desired thickness and thermal conductivity. At least one layer of thermally insulating walls of a desired thickness and thermal conductivity is disposed around the at least one row of first containers. The first containers and thermally insulating walls are capable of being immersed from a range of about 5° C. to room temperature directly into a liquid cryogenic fluid below a surface thereof and freezing the sperm, without vitrification, at a cooling rate sufficient to maintain post-thaw quality of the sperm. The cooling rate is controlled solely by the thermal conductivity of the walls of the first containers, the layer(s) of thermally insulating walls and any substance between the walls of the first containers and the at least one thermally insulating container.

17 Claims, 13 Drawing Sheets

(56) References Cited

OTHER PUBLICATIONS

S.I.Moskovtsev et al., Cryopreservation of Human Spermatozoa by Vitrification vs. Slow Freezing: Canadian Experience, www.intechopen.com, 2012.

Zhiquan Shu et al., Development of a Reliable, Low-cost, Controlled Cooling Rate Instrument for the Cryopreservation of Hematopoietic Stem Cells, HHS Public Access, Apr. 12, 2010.

Imv Technologies, MCA & dedicated mobile host tank, brochure, www.imv-technologies.com, 2011.

Thomas Listerman, Cooling by Immersion on Liquid Nitrogen, Wright State University, Jun. 1986.

* cited by examiner

MULTILAYER INSULATION OF BIOLOGICAL SAMPLES AND COOLING BY IMMERSING IN A CRYOGENIC LIQUID FOR CRYOPRESERVATION

This application claims the priority of U.S. provisional patent application No. 62/187,815 filed on Jul. 2, 2015.

BACKGROUND OF THE INVENTION

1. Field of the Invention

The present invention is directed to a method and system for preservation of sperm and other biological samples during freezing when cooling by placing into a cryogen, for example, immersing into liquid nitrogen for cryopreservation.

2. Description of Related Art

Sperm and other biological samples are frozen by slow controlled rate freezers using complex multiple sequential surrounding environments, such combinations of liquid nitrogen vapor and injections of liquid nitrogen. Sperm has also been cooled and frozen in a static liquid nitrogen vapor in a container, but the cooling rate control has been roughly by the height of the sperm straws to the surface of liquid nitrogen. Current methods also require sorting and packaging of the frozen samples inside the liquid nitrogen vapor or liquid nitrogen in a post freezing process, a process which imposes much additional work burden, risk of harm to personnel, and risk of decrease sperm quality during the process.

A high rate flash-freezing process known as vitrification has also been used, wherein special cryoprotectants are added to the sperm or other biological samples to decrease the freezing temperature and increase the viscosity, so that instead of crystallizing, the syrupy solution becomes an amorphous ice. Rather than a phase change from liquid to solid by crystallization, the amorphous state is like a "solid liquid", and the transformation is over a small temperature range described as the "glass transition" temperature. Such processes are complex and often result in low quality sperm after thawing because of cooling rate and other problems.

SUMMARY OF THE INVENTION

Bearing in mind the problems and deficiencies of the prior art, it is therefore an object of the present invention to provide an improved method and system of freezing sperm and other biological samples which reduces complexity of the materials and processes employed.

It is another object of the present invention to provide a method and system of freezing sperm which carefully controls cooling rate during the freezing process.

A further object of the invention is to provide a system for freezing sperm which employs improved and easy-to-use containers for the sperm suspension.

It is yet another object of the present invention to provide a method for determining optimum cooling rate during freezing of sperm which may be readily replicated.

Still other objects and advantages of the invention will in part be obvious and will in part be apparent from the specification.

The above and other objects, which will be apparent to those skilled in the art, are achieved in the present invention which is directed to a method of cryopreservation of sperm comprising providing a liquid suspension of sperm to be frozen, placing the liquid suspension of sperm in one or more first containers having walls of a desired thickness and thermal conductivity, and placing the one or more first containers in at least one insulating container having thermally insulating walls of a desired thickness and thermal conductivity. The first containers are arranged within the at least one thermally insulating container. The method then includes providing a liquid cryogenic fluid, immersing the at least one thermally insulating container with the first containers containing liquid suspension of sperm from range of about 5° C. to room temperature directly into the liquid cryogenic fluid, the first containers being below a surface thereof, and freezing the sperm, without vitrification, at a cooling rate sufficient to maintain post-thaw quality of the sperm. The cooling rate is controlled solely by the thermal conductivity of the walls of the one or more first containers, the walls of the at least one thermally insulating container and any substance between the walls of the one or more first containers and the at least one thermally insulating container.

A plurality of first containers may be arranged within the at least one thermally insulating container side-by-side in at least one row. The plurality of first containers may be arranged within the at least one thermally insulating container in a single row arrayed around a central axis, within the at least one thermally insulating container in a single straight row, or within the at least one thermally insulating container in a pair of adjacent, straight rows. The at least one thermally insulating container may include a thermally insulating pocket adjacent ends of the straight row(s) of first containers.

The method may include a plurality of first containers and at least two thermally insulating containers, wherein a second thermally insulating container containing the at least one row of a plurality of first containers is placed inside a third thermally insulating container, with the second and third thermally insulating containers having thermally insulating walls of a desired thickness and thermal conductivity. The plurality of first containers may be arranged within the at least one thermally insulating container to each have comparable cooling rates during freezing of the sperm. The cooling rate of the sperm may be controlled to be between about −10 and about −60° C. per minute.

In another aspect, the present invention is directed to a container system for cryopreservation of sperm comprising one or more first containers containing liquid suspension of sperm to be frozen, first containers having walls of a desired thickness and thermal conductivity, the one or more first containers being arranged side-by-side in at least one row, and at least one layer of thermally insulating walls of a desired thickness and thermal conductivity around the at least one row of first containers. The at least one row of first containers and at least one layer of thermally insulating walls may be capable of being immersed from range of about 5° C. to room temperature directly into a liquid cryogenic fluid below a surface thereof and freezing the sperm, without vitrification, at a cooling rate sufficient to maintain post-thaw quality of the sperm. The cooling rate is controlled solely by the thermal conductivity of the walls of the first containers, the at least one layer of thermally insulating walls and any substance between the walls of the first containers and the at least one thermally insulating container.

The container system may have a plurality of first containers arranged within the at least one layer of thermally insulating walls in a single row arrayed around a central axis, in a single straight row, or in a pair of adjacent, straight rows. The container system may further include, within the at least one layer of thermally insulating walls, a thermally insulating pocket adjacent ends of the straight row(s) of first containers.

The container system may include at least two layers of thermally insulating walls, wherein a first layer of thermally insulating walls is adjacent the at least one row of a plurality of first containers and a second layer of thermally insulating walls is adjacent the first thermally insulating layer, the first and second thermally insulating layers having a desired thickness and thermal conductivity. The plurality of first containers may be arranged within the at least one layer of thermally insulating walls to each have comparable cooling rates during freezing of the sperm.

The container system may have a plurality of first containers arranged within the at least one layer of thermally insulating walls in a pair of adjacent, straight rows and include at least two layers of thermally insulating walls. A second layer of thermally insulating walls may be adjacent the at least one row of a plurality of first containers and comprise a polymeric box. A third layer of thermally insulating walls may be adjacent the second thermally insulating layer and comprise a polymeric bag. The first, second and third thermally insulating layers have a desired thickness and thermal conductivity. The container system may further include additional thermally insulation between the first and second layers of thermally insulating walls and adjacent ends of the straight rows of first containers.

In a further aspect the present invention is directed to a method of determining optimal cooling conditions for cryopreservation of sperm comprising providing a liquid suspension of sperm to be frozen, dividing the liquid sperm suspension into a plurality of different portions, and placing the liquid sperm suspension portions into a one or more first containers having walls of a desired thickness and thermal conductivity and positioned within thermally insulating walls of a desired thickness and thermal conductivity. Each of the liquid sperm suspension portions may have different degrees of thermal insulation in their respective first container within thermally insulating walls. The method also includes providing liquid cryogenic fluid, immersing the liquid sperm suspension portions in their respective first container within thermally insulating walls from range of about 5° C. to room temperature directly into the liquid cryogenic fluid, and freezing the sperm suspension portions, without vitrification, until the sperm suspension portions are frozen. The cooling rate of the sperm suspension portions may be controlled solely by rate of heat flow to surrounding liquid cryogenic fluid through the walls of its respective first container, the thermally insulating walls and any substance between the walls of the first container and the thermally insulating walls. The different sperm suspension portions may be subject to a plurality of different cooling rates. The method further includes thawing the sperm suspension portions, determining quality of the thawed sperm suspension portions and, for thawed sperm suspension portions determined to have desired quality, identifying the type of first container and thermally insulating walls used for the thawed sperm suspension portions determined to have desired quality. The method then includes placing additional sperm suspension to be frozen in first containers in the same type of first container and thermally insulating walls used for the thawed sperm suspension portions determined to have desired quality, and subjecting the additional sperm suspension to the same rate of cooling by immersing the additional sperm suspension directly into the liquid cryogenic fluid to freeze, without vitrification, such additional sperm suspension.

The method may further including measuring cooling rate of the sperm suspension portions during freezing, and determining acceptable cooling rate for thawed sperm suspension portions determined to have desired quality.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1-21 of the drawings in which like numerals refer to like features of the invention.

Figure 1:
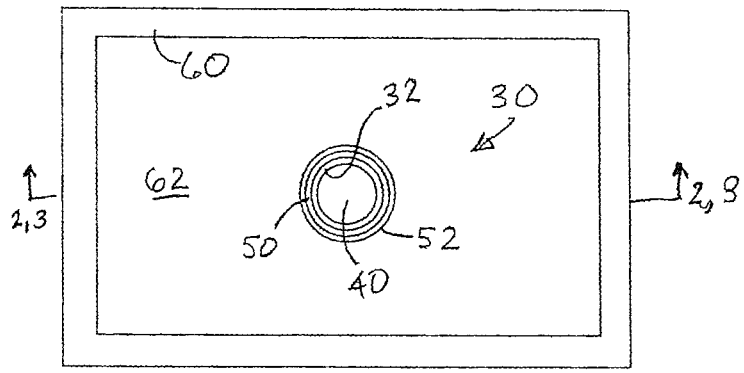
FIG. 1 is a cross-sectional view of one embodiment of the freezing container system of the present invention, taken normal to the longitudinal axis of the system, employing a first insulation and packaging container(s) holding a sperm suspension, surrounded by thermally insulating walls.
Figure 2:
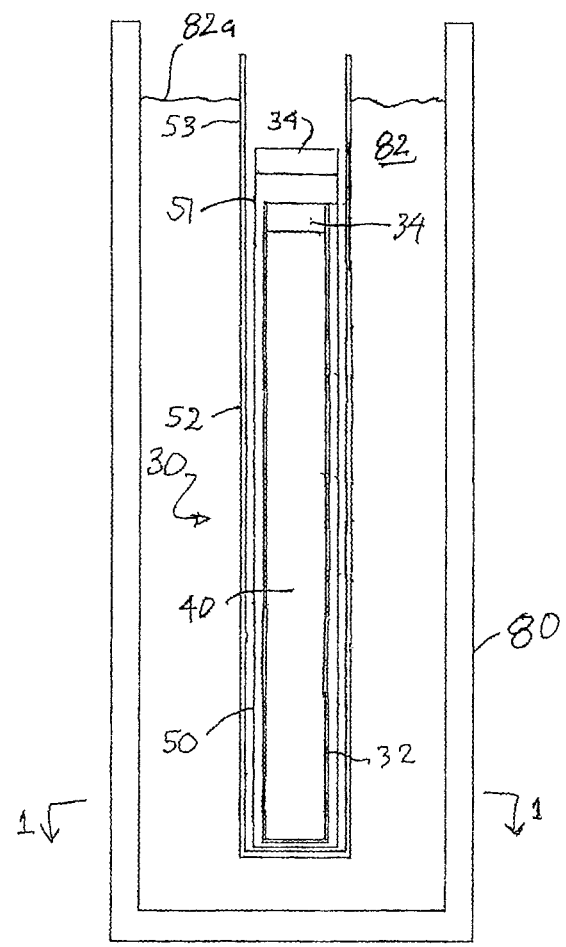
FIG. 2 is an elevational cross-sectional view, along line 2-2, of one example of the freezing container system of FIG. 1 employing a single first insulation and packaging container.
Figure 3:
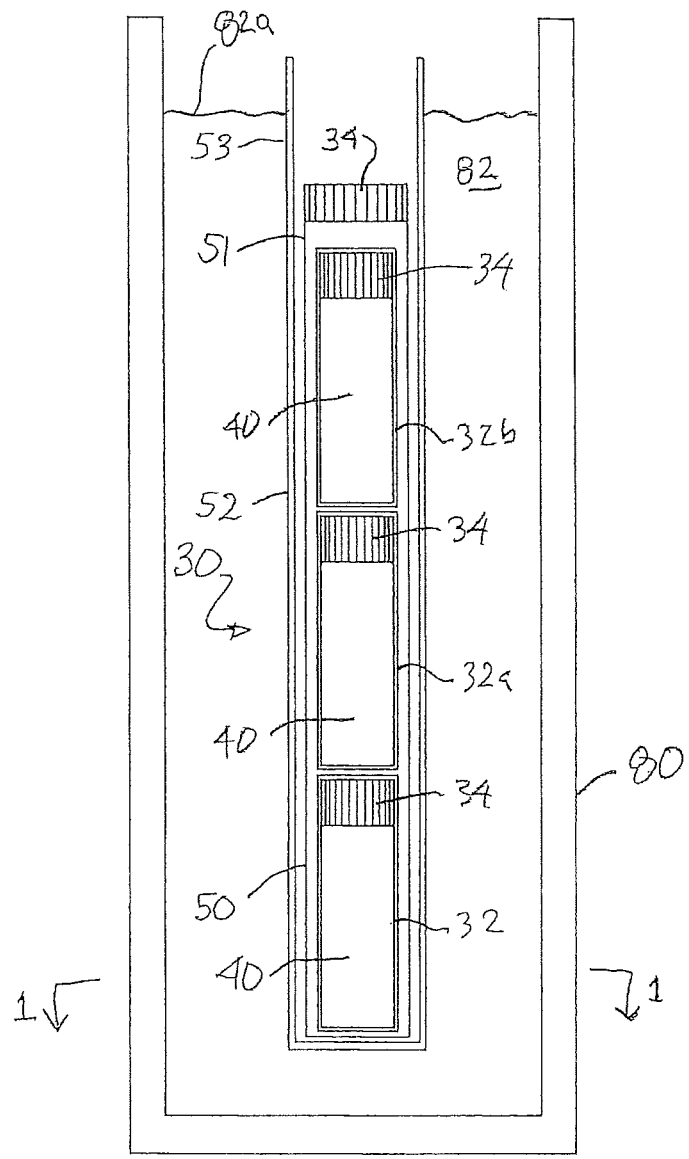
FIG. 3 is an elevational cross-sectional view, along line 3-3, of another example of the freezing container system of FIG. 1 employing a three coaxial, stacked first insulation and packaging containers.
Figure 4:
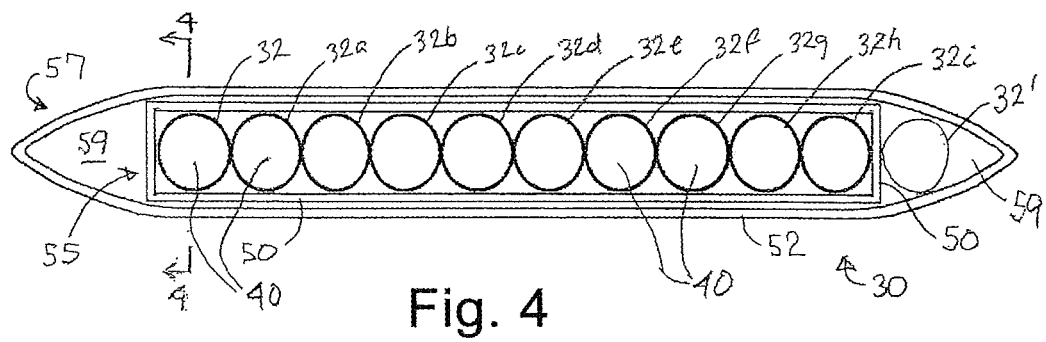
FIG. 4 is a cross-sectional view of another embodiment of the freezing container system of the present invention employing a single row of first insulation and packaging containers holding a sperm suspension, surrounded by thermally insulating walls.
Figure 5:
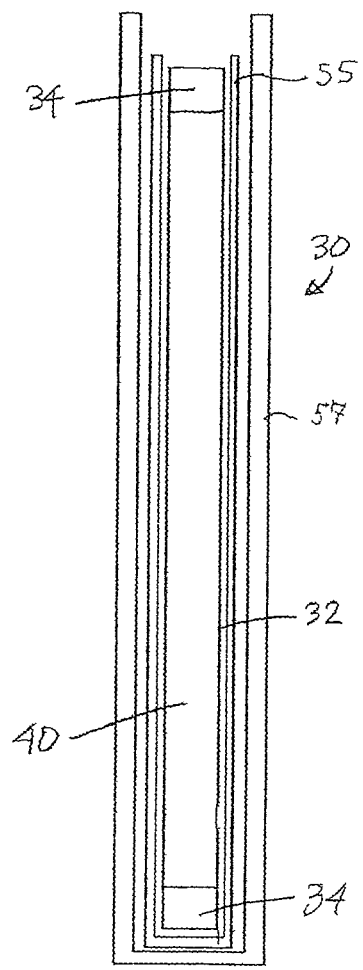
FIG. 5 is an elevational cross-sectional view, along line 4-4, of the freezing unit of FIG. 4.

FIGS. 1, 2 and 3 show examples of the freezing container system of the present invention, in which container system 30 comprises at least one first container 32 partially or fully filled with a liquid suspension of sperm 40 to be frozen. In the embodiment depicted in FIG. 2, first container 32 comprises a single tube such as a plastic straw otherwise conventionally used sperm storage and dispensing. The tube is shown as being circular in cross-section, but it may be any other cross-sectional configuration such as square, rectangular, polygonal and the like. In the embodiment depicted in FIG. 3, three (3) closed bottom glass or plastic vials 32, 32a, 32b are partially filled with the sperm suspension 40, and are each sealed at the upper end by cap 34. Such vials may be of any length and width (diameter), and any desired capacity, for example, 1.8 ml. The first container 32 as described herein may be the primary container contacting the sperm suspension, and may be the final storage container in which the sperm suspension is in direct contact and in which the frozen sperm suspension will be stored for a desired (or indeterminate) period of time. Use of such first or final storage containers and second layer insulation and packaging container eliminates the need to transfer the frozen sperm suspension in first container to another primary container following the freezing process herein. The first container 32 may also be the container in which the sperm is thawed, and from which the sperm is dispensed for fertilization or further testing. Other types of first containers may be employed. The first containers have walls of a desired thickness and thermal conductivity, which will be employed in the process of the present invention.

As seen in FIG. 3, the sealed vials 32, 32a, 32b are cylindrical in configuration, and are stacked end-to-end, on top of one another to create an array of sealed first containers of the sperm suspension. The first container(s) 32 may be of any length, and of any other desired cross-sectional configuration, such as oval, square or rectangular in cross-section. The one or more first containers 32 are surrounded by at least one additional wall or layer of thermally insulating material, and two such additional walls or layers 50, 52 are shown in FIG. 1. The combination of first container(s) and any additional thermally insulating walls 50 and/or 52 may be referred to as an insulation unit. When sperm suspension is placed in the first container(s), it is then referred to a freezing unit. The sperm suspension in the first container and at least the second container having insulating walls 50 may then be used to store the frozen sperm suspension.

In accordance with the method of the present invention, the type of material, thickness, and thermal conductivity of the walls of the first containers, any additional layer(s) 50, 52 and any substance such as air between the layers are selected so that, when the first container(s) and any additional surrounding thermally insulating layers are immersed in a liquid cryogenic fluid, the cooling rate experienced by the sperm suspension in the first containers is sufficient to maintain post-thaw quality of the sperm. The first container(s) 32 and at least the second thermal insulation layer 50 of the insulation or freezing unit may have functions of insulation, packaging, sorting, storage and protection for the sperm suspension disposed within. The third layer of the insulation or freezing unit, 52, may be sealed and used for storage also, or may be removed as not necessary for storage.

The term liquid cryogenic fluid refers to a fluid that is in liquid form at temperatures below −180° C. (−292.00° F.) or 93.15° K. This includes permanent gases such as helium, hydrogen, neon, nitrogen, oxygen, and normal air, which have normal boiling points that lie below −180° C. The term sperm quality refers to sperm motility, acrosome integrity and other indices of the ability of the sperm to fertilize an egg or oocyte, after freezing, particularly to the temperature of liquid cryogens such as liquid nitrogen ($LN_2$) at −196° C. The cooling rate to maintain post-thaw quality of the sperm may differ by species, by strain or even by individual ones of sperm being frozen. For human and some other animal sperm, the desired cooling rate may be in the range of between about −10 and about −60° C. per minute.

This multilayer insulation unit is shown in FIGS. 1, 2 and 3 with three (3) layers of insulation containers. Sperm suspension 40 is first packaged and insulated by the first containers 32, 32a, 32b, and then the sperm suspension within the first insulation containers is further packaged and insulated by the second layer 50 of insulation container 51. FIGS. 2 and 3 shows wall or layer 50 to be part of a larger diameter thermally insulating tube or vial 51 into which tube 32 (FIG. 2) or vials 32, 32a, 32b (FIG. 3) slide. The sperm suspension is further insulated by the third insulation layer 52 of container 53. Tube or vial 51 is itself slidingly fitted within flexible or rigid tube 53 having thermally insulating wall or layer 52. In the event that there is spacing between the first containers and any additional layer(s), such as by one or more air layers, the thermal conductivity (including convection) properties of any intermediate substance contributes to the cooling rate of the sperm suspension. The insulation units 30 shown in FIGS. 2 and 3 show five (5) insulation layers, i.e., three (3) insulation container layers and two (2) insulation layers filled with air.

In the method of freezing the sperm suspension in accordance with the present invention, a container 80 such as a tank, styrofoam box or dewar is provided and filled with a bath of the liquid cryogenic fluid 82, e.g., $LN_2$, to a sufficient height to cover the top of the first container of sperm suspension. The vertically oriented container system 30 of first container(s) and surrounding insulating layer(s), which may be normally in the range of about 5° C. to room or ambient temperature, is directly plunged and immersed into the liquid cryogenic fluid so that the top of the first container of sperm suspension is below the upper surface 82a of the liquid cryogen. Thermally insulating layers 50, 52 should be sealed to prevent inflow of liquid cryogen, at least along the portions below the liquid cryogen surface. The layers 50, 52 may be have open upper ends above the surface of the liquid cryogen, as with tube 53, or may be completely sealed, as with vial 51. The outer layers are completely sealed, they may be fully immersed below the surface of the liquid cryogen. Any desired number of first containers may be stacked together as shown in FIG. 3, or alternatively a single longer container may be employed.

As the sperm suspension is cooled, it freezes in a one-step freezing procedure, without vitrification, at a cooling rate sufficient to maintain post-thaw quality of the sperm. The cooling rate is controlled solely by the thermal conductivity of the walls of the first container(s), the walls of the surrounding thermally insulating container(s), and any substance between such walls. The number, thickness and material of the walls of the first container and surrounding thermally insulating layers may be determined by experimentation to ensure post-thaw sperm quality, and will be discussed further below.

As an alternative to the single row of one first container in FIGS. 1, 2 and 3, FIGS. 4 and 5 depict a plurality of first containers 32, 32a, 32b, 32c, 32d, 32e, 32f, 32g, 32h, 32i arrayed in a single straight row. In this example, the first containers are plastic straws sealed with a heat sealer, a metal or glass ball or cotton plug 34. The straws used for the first container in this and other examples herein may be of any desired length, diameter, wall thickness and capacity, for example, Mini straws of 133 mm length, 2 mm outer diameter, 0.2 mm wall thickness and 0.25 ml capacity. Other sizes may be used, such as Medium straws 0.5 ml capacity (133 mm length, 3 mm outer diameter, 0.2 mm wall thickness) or Macro straws of 5 ml capacity (280 mm length, 6 mm outer diameter 0.3 mm wall thickness). First containers 32-32i are shown as being cylindrical in cross section, but they may be of any cross section that has at least one line of symmetry, wherein the line is arrayed along the length of a straight or curved row of first containers. The row of first containers is shown within rigid plastic box 55 having thermally insulating side walls 50 surrounding the length of the straws, which box is itself contained within flexible bag 57 having thermally insulating side walls 52. To ensure that the sperm suspensions in end containers 32, 32i have similar cooling rate to those containers 32a-32h having containers on each side, there may be provided additional thermal insulation along the free ends of the row, for example an air pocket 59 that may be formed within one or both of the insulating layer 50, 52, or by an empty container tube 32'.

The straws, vials or other first containers, as well as the surrounding thermally insulating walls and layers, may be made of any desired material suitable for sperm storage and freezing, such as glass or a polymer, e.g., low density polyethylene (LDPE), high density polyethylene (HDPE), polyethylene terephthalate and its copolymers (PET, PETE, PETG, A-PET), expandable polyethlyne (EPE), polyethelene (PE) film, polyvinyl chloride (PVC) or ionomers. The first layer insulation containers, tube like straws and other sperm containers, are commercially available from IMV technology, Minitube and MOFA Company and other sources and they may be made of PETG, PVC, LDPE or HDPE. For the thermally insulating layers 50, 52 and additional outer layers, any other materials may be used, such as foams, fabrics or bubble wraps with air pockets. Wood, metals, alloys, ceramics or composites may be used if the thermal insulation properties are acceptable. The flat rigid rectangular box is preferably made of LDPE, PVC or HDPE. The flexible bag is preferably made of EPE or PE film. The materials may be selected on the basis of their thermal insulating properties to achieve the desired cooling rate upon immersion in the liquid cryogenic fluid.

Figure 6:
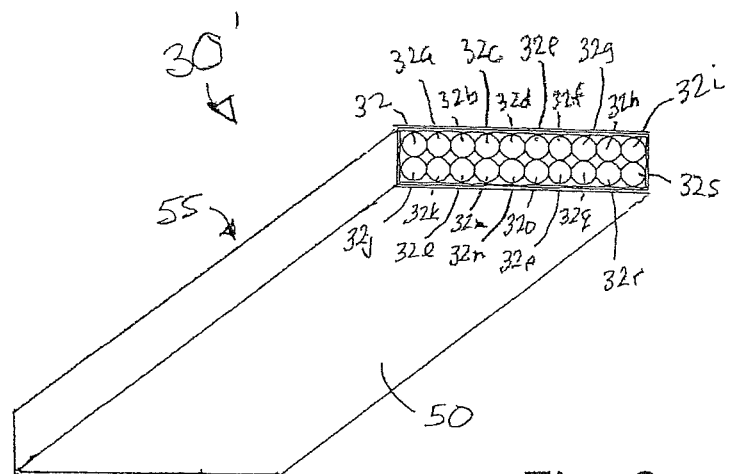
FIG. 6 is a perspective view of another embodiment of the freezing container system of the present invention employing two rows of first layer insulation and packaging containers holding a sperm suspension, within a flat rectangular box having thermally insulating walls.

A double or pair of straight rows of first containers are shown in the example of FIGS. 6, 7, 8 and 9, wherein ten (10) first containers comprising straws 32, 32a, 32b, 32c, 32d, 32e, 32f, 32g, 32h, 32i in one row are arrayed adjacent to and in contact with ten (10) first container straws 32j, 32k, 32l, 32m, 32n, 32o, 32p, 32q, 32r, 32s in a second row. First containers 32a, 32b, 32c, 32d, 32e, 32f, 32g, 32h, 32k, 32l, 32m, 32n, 32o, 32p, 32q and 32r each abut three (3) other adjacent containers, and end containers 32, 32i, 32j and 32s each abut two (2) other adjacent first containers and an end air pocket 59 or other thermal insulation. As with the previous example, the rows of first containers are received within rigid plastic box 55 and flexible bag 57. In the example of a plastic box 55 as shown in FIG. 6, the outer diameter of the straws 32-32s is 2 mm and the length is 133 mm, and the inner dimensions of the box holding 2 adjacent rows of 10 straws are about 4 mm×20 mm, and the length is at least 133 mm, forming a two-layer insulation unit 30'. The bag 57 may be selected with dimensions to fit over box 55, and has opposing seams 57a to permit an air pocket 59 (FIG. 8) or additional tube (32' as in FIG. 4) at each end of box 55 for additional insulation for the end containers 23, 32i, 32j and 32s. The thickness of the walls 50 of box 55 and walls 52 of bag 57, forming a three-layer insulation unit, may be selected as desired to obtain the desire cooling rate for the sperm suspension in containers 32-32s. Each container 32-32s is separated by only the layers of the surrounding insulating layers 50, 52 from the liquid cryogenic fluid, so that each container has similar cooling rates upon immersion. If outer thermally insulating layer 52 is left open at the top, the top should remain above the surface 82a of the cryogen liquid 82. If the top of thermally insulating layer 52 is sealed 34', such as by heat or other sealing applied to the end of bag 57, the entire bag 57 may be immersed below the cryogenic liquid surface 82a'.

Figure 7:
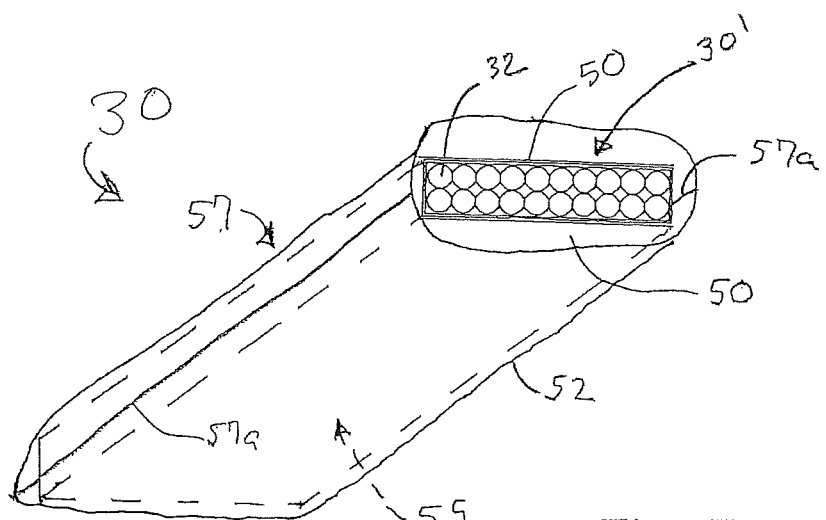
FIG. 7 is a perspective view of the two rows of first layer insulation and packaging storage containers within a rectangular box of FIG. 6, further held within a bag having thermally insulating walls.
Figure 7A:
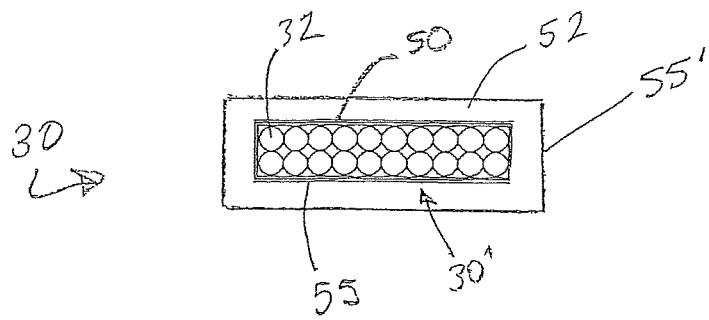
FIG. 7a is a cross-sectional view of the two rows of first layer insulation and packaging containers within a rectangular box of FIG. 6, further held within rectangular foam box or plastic box having thermally insulating walls.

Instead of using a flexible bag 57 around the first containers and box 55 layers 50 of insulation unit 30' shown in FIG. 7, insulation unit 30' may be placed in and surrounded on its sides by a foam box or rigid plastic box 55' as shown in FIG. 7a. The walls 52 of foam box or rigid plastic box 55' may be selected to provide the desired cooling rate to the first containers in box 55.

Figure 10:
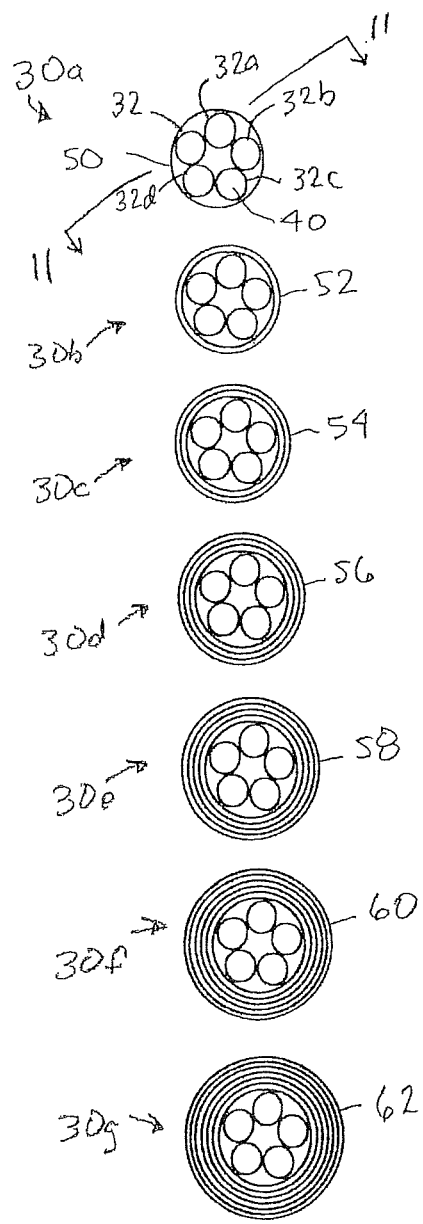
FIG. 10 is a cross-sectional view of another embodiment of the freezing container system of the present invention employing first layer insulation and packaging containers arranged in a circular array within different numbers of layers of tubes having thermally insulating walls.
Figure 11:
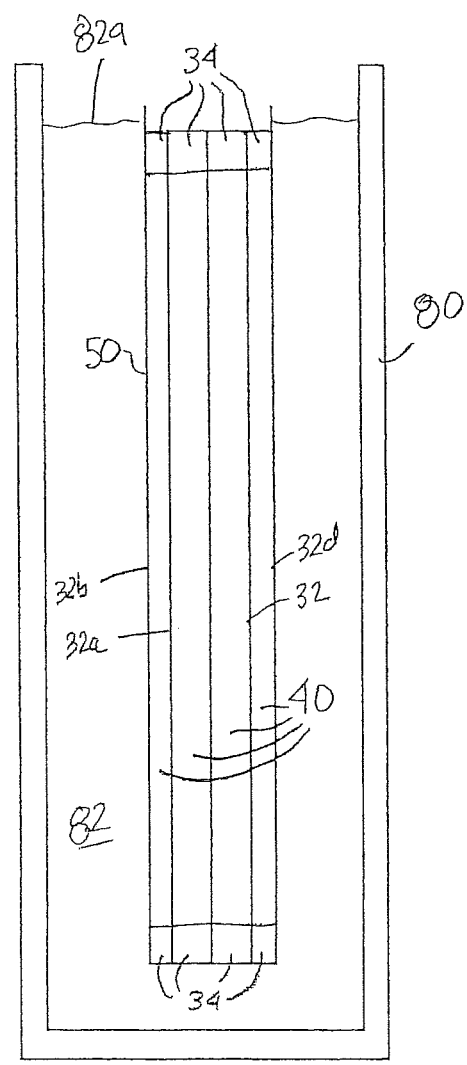
FIG. 11 is an elevational cross-sectional view, along line 11-11, of one of the freezing container systems of FIG. 10.
Figure 12:
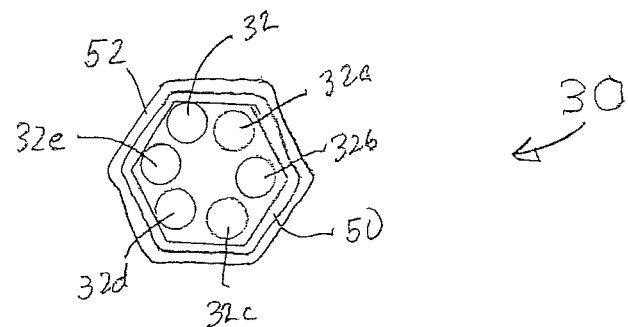
FIG. 12 is a cross-sectional view of an alternate embodiment of the freezing container system of FIG. 10 having the first layer insulation and packaging containers arranged in a polygonal array within layers of tubes having thermally insulating walls.
Figure 13:
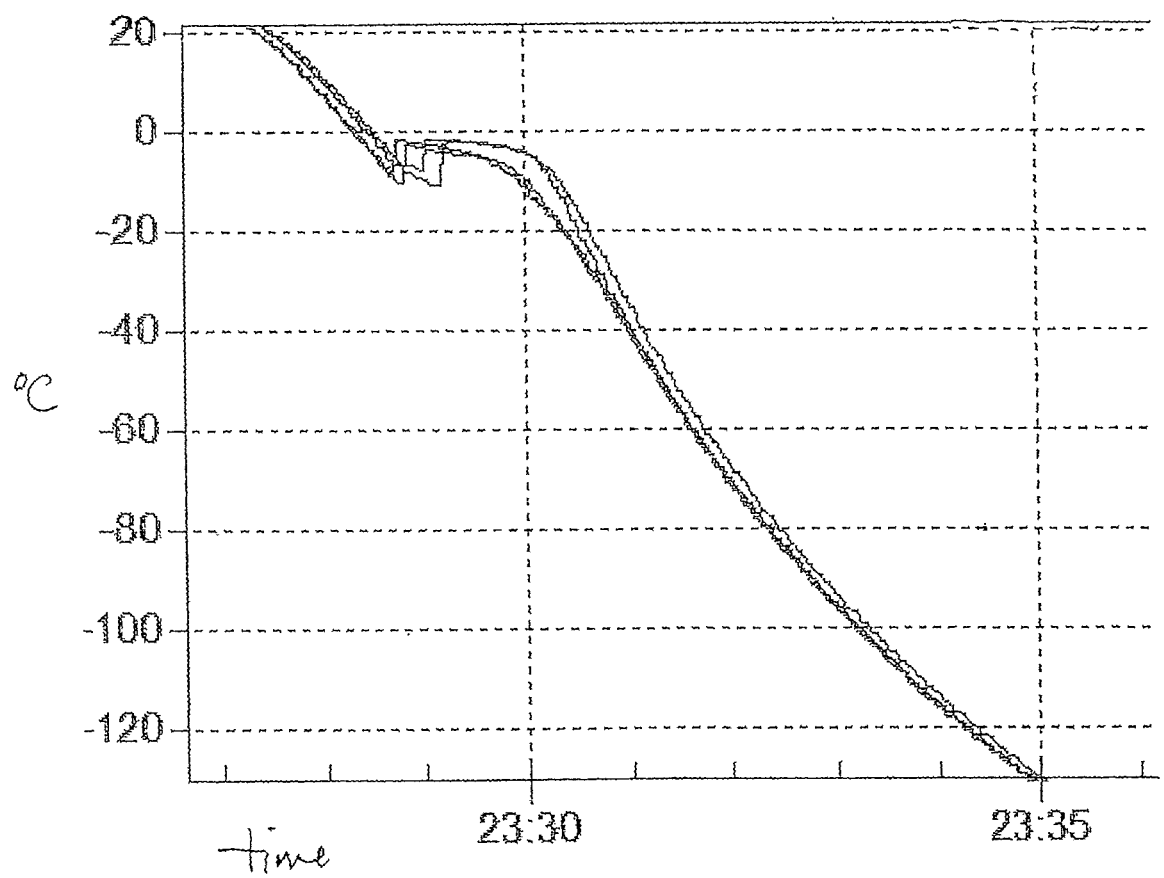
FIG. 13 is a graphical representation of the cooling rates of sham liquid samples during freezing of the insulation and packaging container systems of FIG. 10 in accordance with the present invention.

A single row of first containers 32, 32a, 32b, 32c, 32d may also be arrayed in a circular or other configuration in which the containers are arrayed around a central longitudinal axis so that there is no free end to the row, as shown in FIGS. 10 and 11. The circularly-arranged row may have at least three (3) first containers, and may have more than the five (5) first containers shown. As an alternative to the circular arrangement, the first containers may have other configurations about a central axis, such as the hexagonal array shown in FIG. 12. The flexible or rigid thermally insulating layer may be of multiple layers or walls of closely fitting dimension, or may be a single layer or wall of different desired thicknesses. Starting with insulation unit 30a an additional thermally insulating layer is added for each of subsequent insulation units 30b, 30c, 30d, 30e, 30f and 30g. The surrounding thermally insulating layers 50, 52 (FIG. 12) or 50, 52, 54, 56, 58, 60, 62 (FIG. 10) may be flexible or rigid tubes, vials or bags of closely fitting dimension as shown. Each first container within inner thermally insulating layer 50 is adjacent and in contact with two (2) other first containers, and is separated by only the layers of the surrounding insulating walls from the liquid cryogenic fluid, so that each first container has similar cooling rates upon immersion therein. The surrounding thermal insulation layers may also have air spacing between one or more layers, to also achieve similar cooling rates. An example was tested with temperature sensor in each first container 32, 32a, 32b, 32c, 32d, and showed essentially the same acceptable cooling rates when undergoing freezing in $LN_2$, as shown in FIG. 13.

Figure 14:
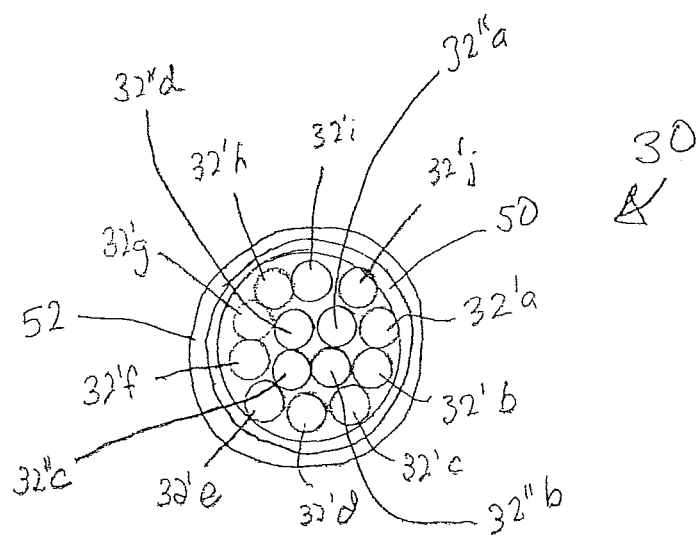
FIG. 14 is a cross-sectional view of an another embodiment of the freezing unit of FIG. 10 having the first layer insulation and packaging containers arranged in a multiple circular rows within layers of tubes having thermally insulating walls.

In another embodiment of insulation unit 30 shown in FIG. 14, tubular first containers may be arranged in two rows around a central axis, wherein containers 32'a, 32'b, 32'c, 32'd, 32'e, 32'f, 32'g, 32'h, 32'l and 32'j are arrayed in an outer row and containers 32"a, 32"b, 32"c and 32"d are arrayed in an inner row. Because inner row containers 32"a-32"d do not receive the same cooling rate as outer row containers 32'a-32'j, both rows of containers may receive sperm suspension to be frozen only if both cooling rates are within the range of acceptable cooling rates for post-thaw quality of the species of sperm being frozen. Alternatively, sperm solution may be placed in one of the inner or outer rows, and the other of the inner or outer rows left empty. If the sperm suspension is placed in the inner row containers 32"a, 32"b, 32"c and 32"d, the outer row containers 32'a, 32'b, 32'c, 32'd, 32'e, 32'f, 32'g, 32'h, 32'l and 32'j act as a thermal insulation layer.

Figure 15:
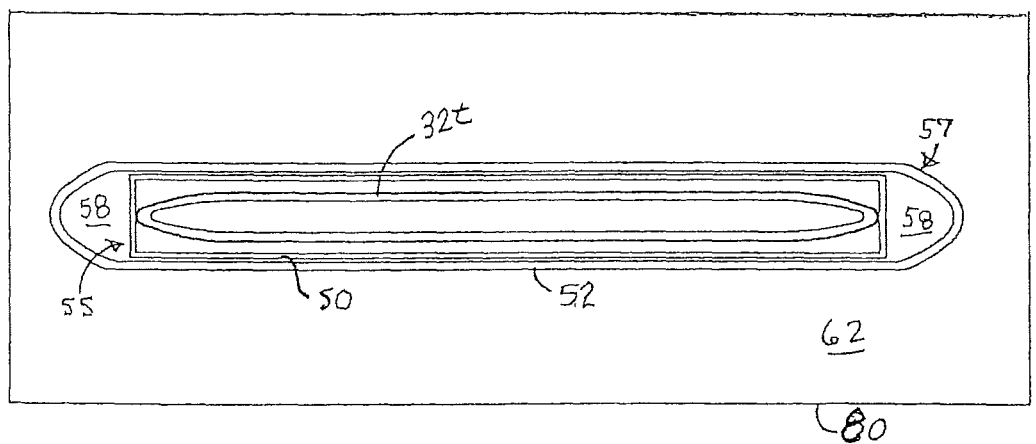
FIG. 15 is a cross-sectional view of another embodiment of the freezing unit of the present invention employing an elongated flexible bag as the first layer insulation and packaging storage container within a rigid box and flexible bag having thermally insulating walls.

A single, non-round, elongated oval cross-section for first container 32t is shown in FIG. 15. This may be, for example, a plastic bag. The length, minor diameter and major diameter of the first container may be any desired, and the surrounding thermal insulating layers 50, 52 are sized to provide a desired fit to create the desired insulation unit 30. A pair of such first containers 32t may be abutted along their longer sides, to create a two-row insulation unit analogous to that shown in FIGS. 6-8. While first container 32t may be a semen bag, other types of containers may be used such as a blood bag. The use of a rigid box 55 as the second thermal insulation layer 50 is useful since its dimension may be selected to ensure that the thickness of sperm suspension in bag 32t does not exceed a desired dimension, such as 2 mm, so that desired cooling rate is achieved for the sperm suspension inside. Typically, the bag has a capacity of 10 ml, which can insulate and package 5 ml of sperm suspension of, for example, a boar, stallion or the like.

Figure 8:
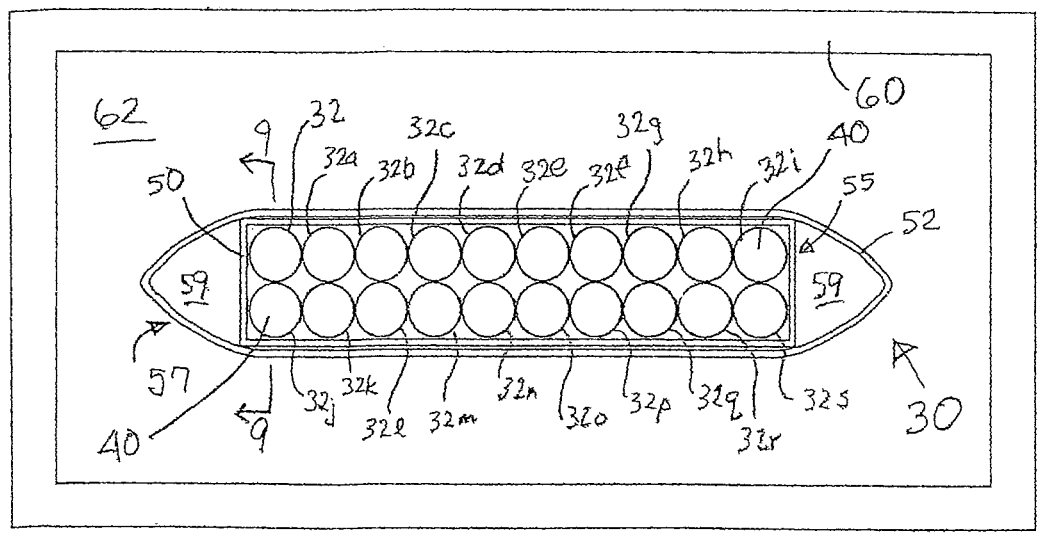
FIG. 8 is a cross-sectional view of the freezing unit of FIG. 7.
Figure 9:
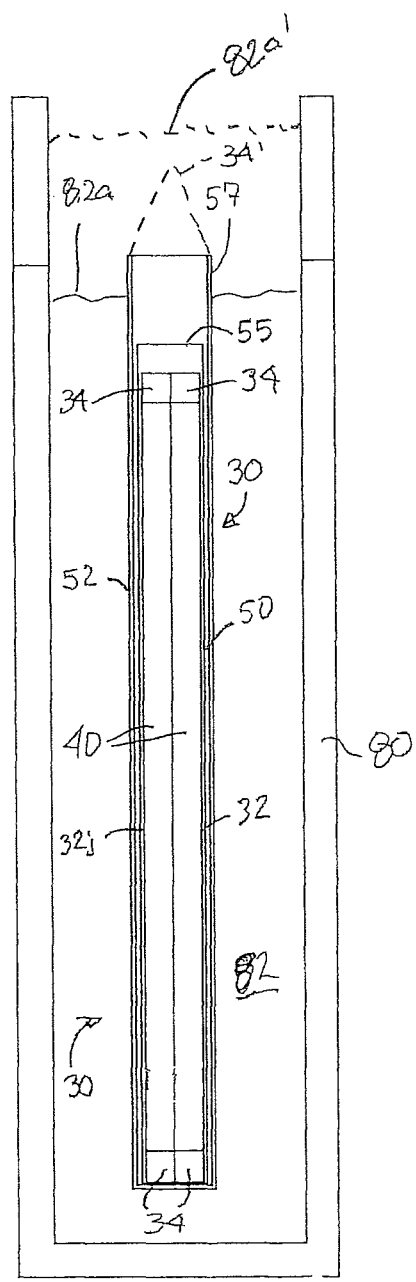
FIG. 9 is an elevational cross-sectional view, along line 9-9, of the freezing unit of FIG. 8.
Figure 16:
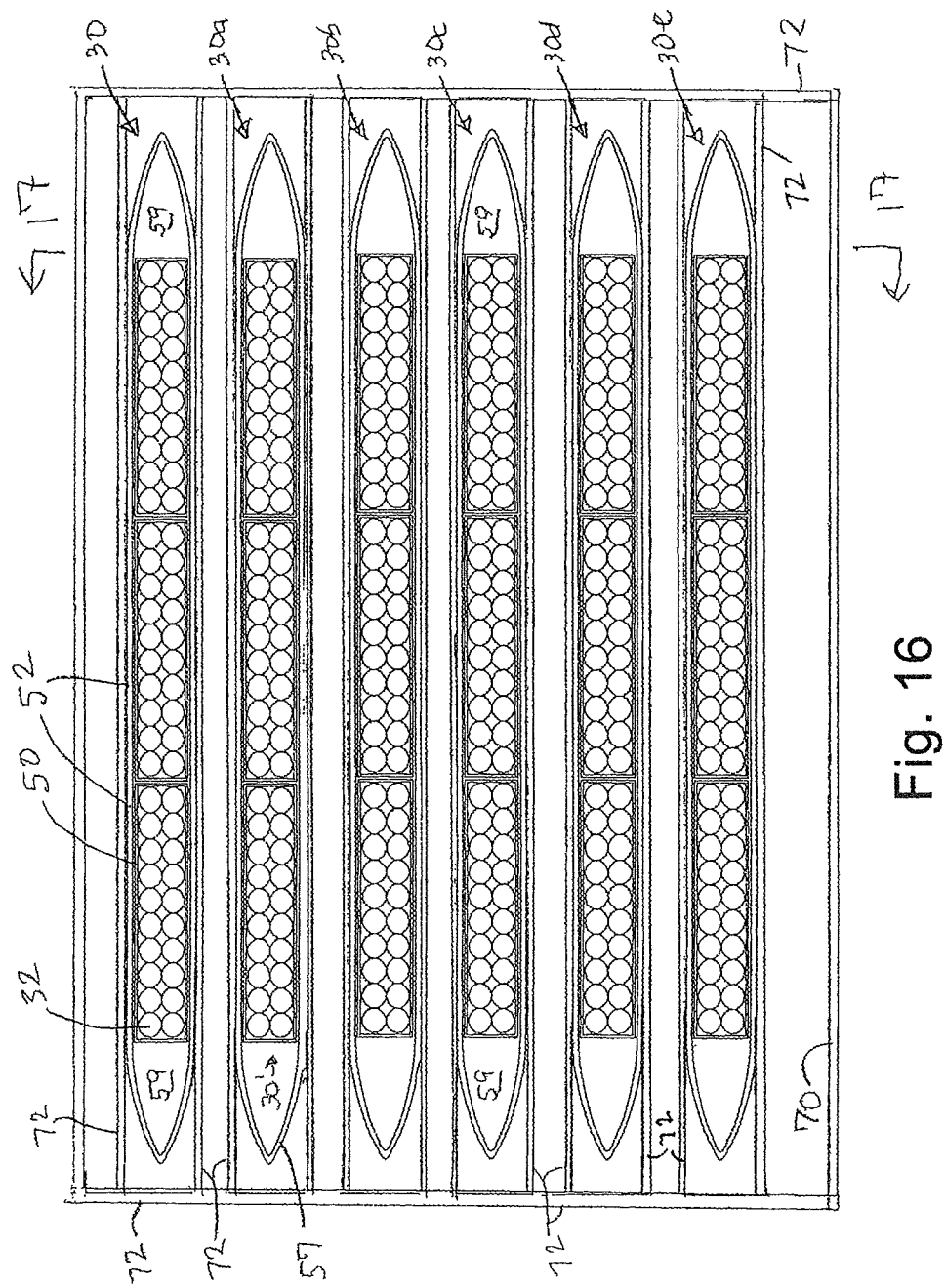
FIG. 16 is a cross-sectional view of a rack holding six freezing units of the present invention, each employing straws as the first layer insulation and packaging container in two rows within three side-by-side rigid boxes of the type of FIG. 6, and disposed within a flexible bag having thermally insulating walls.
Figure 17:
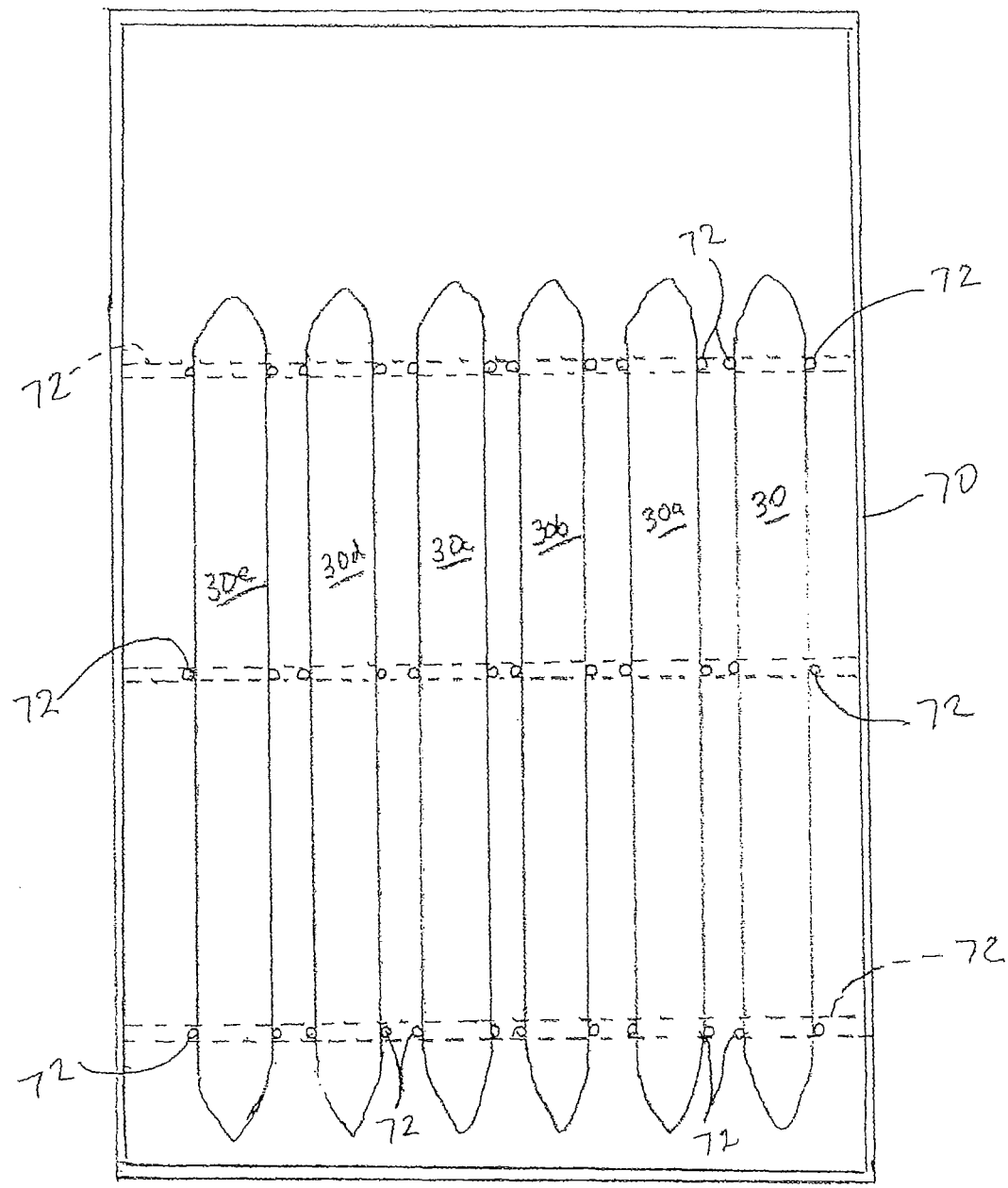
FIG. 17 is an elevational cross-sectional view, along line 17-17, of the rack holding six freezing units of FIG. 16.
Figure 18:
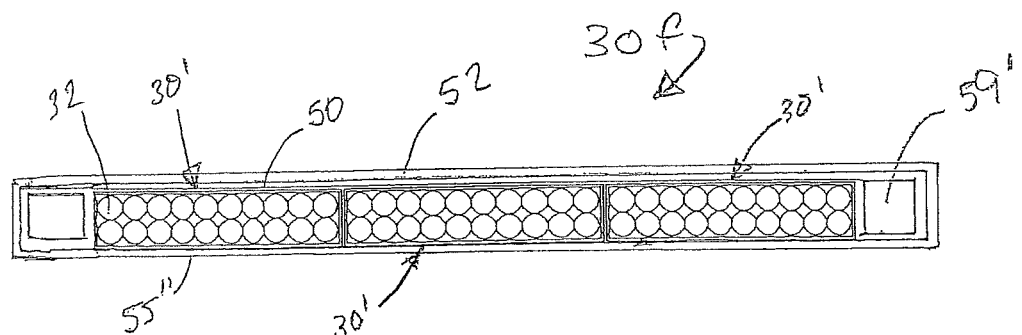
FIG. 18 is a cross-sectional view of a freezing unit of the type of FIG. 16 having foam insulation along the ends of the three side-by-side rigid boxes, and disposed within a rigid box having thermally insulating walls.

While first container(s) in single storage array 30 are depicted in the examples above, the present invention may employ two or more spaced arrays for direct immersion into the liquid cryogenic fluid. As depicted in FIGS. 16 and 17, six (6) arrays 30, 30a, 30b, 30c, 30d, 30e of flexible bags 57 each holding three of the boxed, double row type insulation units 30' of first containers of sperm suspension of FIGS. 6-8 are shown. Instead of flexible bags 57, the insulation units 30' may be received within larger insulating box 55", with either air pockets or foam blocks 59' at the opposite ends forming a insulation unit 30f as shown in FIG. 18. Either arrays 30-30e and/or 30f may be held in spaced relationship by rods 72 in a rack 70 or other structure. Adjacent storage arrays should be spaced from one another to ensure that there is sufficient liquid cryogenic fluid between the arrays after immersion to have similar cooling rates for all of the first containers. If, for example, the arrays 30-30e are too close, excessive amounts of liquid cryogenic fluid may boil off in that space, and change the cooling rate of those first containers adjacent that space compared to others where the cryogen remains liquid.

In practice of freezing sperm suspension in accordance with the invention, the desired number of first containers containing the sperm or other biological samples are placed in the desired layer(s) of thermally insulating walls and may be then immersed or plunged directly from a range of about 5° C. to room or ambient temperature into the liquid cryogenic fluid to freeze the sperm suspension. The cooling rate of the sperm suspension in the first containers is controlled solely by the thermal conductivity of the walls of the first container(s), the walls of the thermally insulating container(s) and any substance between such walls. An example of the cooling rate to which the sperm suspension may be subjected in the method of the present invention is shown in FIG. 13, where a sham liquid sample temperature is plotted as a function of time. In the plot shown, the rate of cooling is fairly linear except during the time that the sperm suspension is transitioning from a liquid to a solid. This plateau effect may be diminished or eliminated by employing the type of first container 32t shown in FIG. 15. There is no necessity to move sperm suspension in its container from one cooling device to another, or to control temperature change or cooling rate of the surrounding media in which the sperm suspension is being frozen. By selection of the proper thermally insulating layers, the cooling rate of the sperm may be controlled in one step to maintain post-thaw quality of the sperm, for example, between about −10 and about −60° C. per minute (normally measured between 5° C. and −130° C.), or any other acceptable cooling rate for the particular species of sperm. A total of three to four layers of thermal insulation may be sufficient to achieve this cooling rate. While some species such as mouse sperm may have acceptable post-thaw quality within this entire range, in other species such as some fish species a difference of 5° C. in cooling rate may result in an adverse change in post-thaw sperm quality. The cooling rate employed in the method of freezing under the present invention is generally less than 100° C. per minute, and may be less than 75° C. per minute, which is considerably slower than vitrification.

Figure 20:
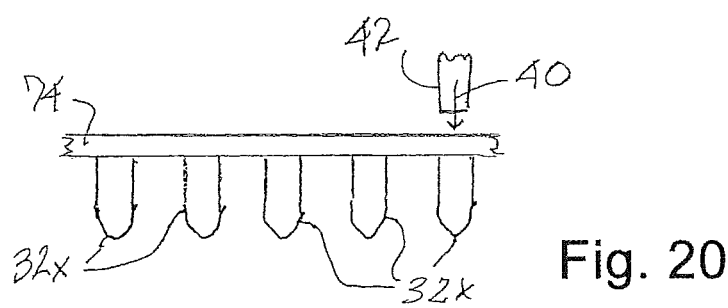
FIG. 20 is an elevational view of another embodiment of the container system of the present invention having a plastic frame holding individual first containers indexing and filling with sperm suspension.
Figure 21:
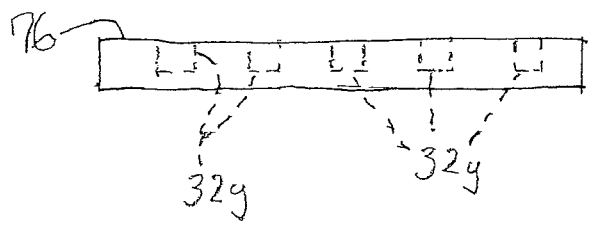
FIG. 21 is an elevational view of another embodiment of the container systems of the present invention in which first containers are drilled or formed out of a block or sheet to form individual spaced containers for receiving sperm suspension

The first containers holding sperm suspension may also be constructed for automated dispensing and testing. In FIG. 20 the first containers are of the type known as PCR tubes, in which a plastic frame 74 holds individual containers 32x that may be indexed and filled with sperm suspension 40 by a dispensing spout 42. The containers may also be drilled or formed out of a block or sheet 76 to form individual spaced containers 32y for receiving sperm suspension, as shown in FIG. 21.

The sperm suspension that may be preserved in the container system of the present invention and/or frozen in accordance with the present invention include semen and spermatozoa of humans and animals, including that of fish, dogs, hogs, boar, horses, bulls and transgenic mice and rats. In humans, the sperm suspension may be in the form of semen, and there may be optionally added sperm to the suspension diluents or cryoprotectants as used in otherwise conventional, non-vitrified freezing of sperm, such as glycerol, dimethyl sulfoxide (DMSO) and egg yolk. These additives may be used in animal sperm, and others may be used such as a sugar-containing medium for mice sperm. The present invention may also be used to cryogenically freeze other biological samples, such as the blood cell of humans or animals.

The invention may further be employed to determine optimal cooling conditions for cryopreservation of sperm or other biologic samples in the first instance. The sperm or other biologic samples are separated into one or more aliquot samples and placed into one or more first containers having walls of a desired thickness and thermal conductivity, and then placed in at least one thermally insulating container as described above. In one method, the sperm or other biologic samples are divided into different portions, and each sample portion is placed into a different first container within thermally insulating container(s), i.e., a thermal insulation unit. Each portion of the sperm or other biologic samples has a first container and thermally insulating container(s) having different degrees of thermal insulation, so that each sample will undergo a different cooling rate as it is immersed in the cryogenic liquid. This is shown in FIG. 10, where the sample portions may be divided among the first containers having the different number additional thermally insulating layers. The different sample portions in their respective containers are noted and recorded.

Figure 19:
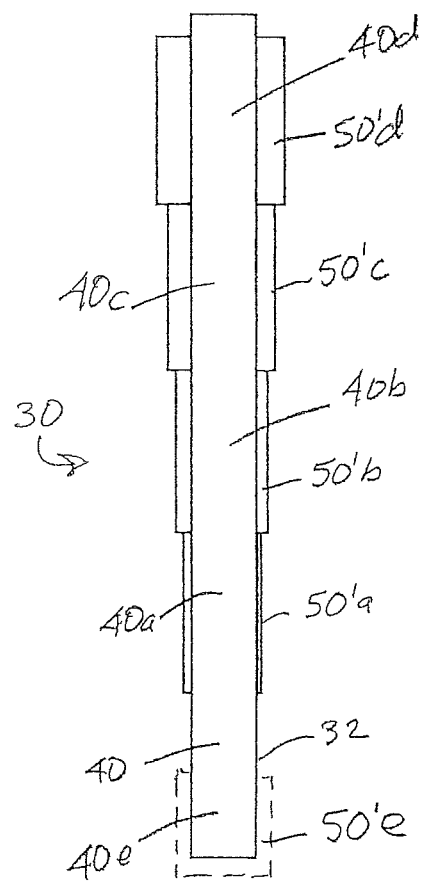
FIG. 19 is a cross-sectional view of a freezing unit of the present invention having straw or tube as a single first container, with different degrees of additional thermal insulation along the length.

The sperm or other biological samples may also be placed in a single or multiple first containers in which the thermal conductivity varies over its length. In FIG. 19, there is shown a single first container 32 in which the thermal conductivity of the wall of thermally insulating tube 50' varies along its length, either by varying the thermal conductivity of the wall material, the number of wall layers, or the thickness of the wall 50'a, 50'b, 50'c, 50'd, 50'e, as shown. Paper tape or the like may be used as wrapping to form the wall layers. Different sperm sample portions 40, 40a, 40b, 40, 40d are positioned along the length of container 32 at the different thermal insulation levels. To determine whether there are particular heat transfer/cooling effects at ends of the first container, additional insulation 50'e may be disposed at an end of container 32, and the sperm sample portion 40e in that area studied.

The sample portions in their different first containers (e.g., FIG. 10) or different positions in a first container (e.g., FIG. 19) are then directly immersed from a range of about 5° C. to room or ambient temperature directly into the liquid cryogenic fluid so that the first container(s) are below the surface of the fluid, and frozen, without vitrification. The cooling rate of the sperm in the sample portions is controlled solely by rate of heat flow to surrounding liquid cryogenic fluid through the walls of the first container(s), the walls of the surrounding thermally insulating container(s) and any substance between the walls thereof. As noted above, the plurality of different sample portions are subject to a plurality of different cooling rates. For the example of the insulation units shown in FIG. 10 immersed simultaneously directly into $LN_2$, the samples in the three layer insulation unit were shown to have a cooling rate of −65.6° C./min., the samples in the four layer insulation unit were shown to have a cooling rate of −26.9° C./min., and the samples in the five layer insulation unit were shown to have a cooling rate of −20.1° C./min. The present invention enables one to test multiple cooling rates for sperm suspension and other biological samples simultaneously in one step.

After being frozen, the sperm sample portions are then thawed, and subject to testing to determining the quality of the thawed sperm in each of the first container(s) or position therein. The warming rate of the sperm suspension may be as fast as possible to ensure good sperm quality after thawing. For those thawed sperm samples determined to have the desired quality, the type of or position in the first container that contained such sperm portion is determined, and the type of first container and thermally insulating container(s) is noted for reproduction. The different cooling rates may be measured in the different first containers during freezing of the sperm to determine the acceptable, and preferably optimal, cooling rate(s) for thawed sperm sample portion determined to have desired quality.

Subsequently, additional sperm or other biologic samples from the same human or animal may be placed in the same type of first container and thermally insulating container(s) determined to have the optimal cooling rate(s) and conditions for the earlier thawed sperm sample determined to have desired quality. These additional sperm or other biologic samples may be subject to the same cryogenic cooling rate and freezing conditions to achieve the same post-thaw quality as the earlier samples. It should be noted that this method of the present invention does not require one to know the actual cooling rate of the sperm suspension to achieve the desired post-thaw sperm quality, although it may be desirable to measure and record such desirable cooling rate.

One or more cryoprotectants may be added to the sperm or other biological samples to be frozen prior to placing the sperm suspension in the first container. However, it is not necessary to add cryoprotectants used for vitrification, since vitrification is not employed in the freezing process of the present invention. Such cryoprotectants may not need to be removed after thawing of the frozen sperm or other biological samples.

In addition to liquid cryogenic fluids, the present invention may be used with other freezing media to freeze the sperm or other biological samples, such as liquid nitrogen vapor or dry ice, i.e., solid $CO_2$.

EXAMPLES

Example 1

The system employs an insulation unit comprising three (3) types or three (3) layers of insulation containers: a first insulation layer of plastic straws, a second insulation layer of a flat straw box, a third insulation layer of a bag. The insulation unit provides insulation to the treated biological sample such as sperm suspension to be cryopreserved. The process is as follows: Fill treated sperm sample into Mini or Medium straws; seal straws by heat seal, metal ball or glass ball seal; place 2 rows of straws into straw box, for example, 10 straws per row (see FIGS. 6, 7, 8, 9); place the straw box into a bag; optionally seal the bag by a heat sealer. The cooling and freezing method is as follows: Immerse the freezing unit into liquid nitrogen inside a container vertically, either completely covered by $LN_2$, if bag sealed on the top, or not completely cover by $LN_2$ if bag not sealed on the top. The straws are under the surface of liquid nitrogen. After about 15 minutes, transfer box and its frozen content to a $LN_2$ Dewar for long term storage. The cooling rate of biological samples is controlled by the amount of layers of the insulation containers and the thermal property of insulation unit.

Example 2

The system employs a first layer of insulation container of glass capillaries, ampoule, glass tubes, Mini, Medium and Macro plastic straws in a one-row arrangement. The insulation unit comprises two layers of additional insulation containers: a second layer of a flat box, and a third layer of a bag. The process for using straws as first insulation container is as follows: Fill treated semen into Mini, Medium, or Macro straws; seal straws; place one row of straws into straw box, for example, 10 straws per row (see FIG. 4); place the straw box into a bag; optionally seal the bag by a heat sealer. The cooling and freezing method is the same as for Example 1.

Example 3

The system employs a first layer of insulation container, a plurality of plastic vials stacked in a one column, symmetrical arrangement, filled with treated biological samples (cells, semen and the like) and sealed with screw caps. Three or more vials are placed into a plastic tube which is sealed with a screw cap or cover cap (see FIG. 3). The tube is placed into an insulation bag. The cooling and freezing method is the same as for Example 1.

Example 4

The system employs a first layer of insulation container a freezing bag (blood bag, flat semen bag), in a one layer, symmetrical arrangement (see FIG. 15). The biological sample inside is boar semen, stallion semen, or the like. The second insulation container is a a flat plastic box of 0.5-2 mm inner thickness. A third insulation container is a bag made of flexible packaging or wrapping material such as EPE (expandable polyethylene, high density film laminated with EPE foam, smooth in one side and protective in other side), PE (polyethylene) film, or PE foam of different thickness and density. The cooling and freezing method is the same as for Example 1 by horizontally or vertically immersing the freezing unit into $LN_2$.

Example 5

The system employs a cooling rate gradient system using as the first insulation container plastic straws (Mini, Medium). The insulating units have from 2 layers of insulation containers to 8 layers of insulation containers, in a manner similar to that shown in FIG. 10. After filling the first containers with a biological sample or sham sample 5 straws of each are sealed and placed into the different number of insulation tubes. The cooling and freezing method is the same as for Example 1, and the cooling rate of biological samples among the 5 straws inside each insulating unit is the same as each other. However, because of the different number of thermal insulating layers, the cooling rate of biological samples among 7 different insulating units is different, 7 and serially different cooling rates are produced in the one-step freezing procedure of the present invention.

Example 6

The system employs a first insulation tube that has a gradient insulation layers of different thickness, density or heat transfer coefficient, as shown in FIG. 19. During cooling and freezing in the same manner as Example 1, a different cooling rate may be produced along the Z axis of the tube.

Example 7

The system employs freezing units each having first insulation containers comprising Mini straws in 2 rows, 10 straws per row, a second insulation container of a flat straw box, with 1 row of 3 boxes; and a third insulation container of a flexible fabric or plastic film bag, or EPE bag. The freezing system consists of 6 freezing units spaced apart in a rack, as in FIGS. 16 and 17. The rack and freezing units are immersed into LN2 in the manner of Example 1, keeping a minimum space among them with the top opening of the bag exposed out in the air, until the samples are frozen.

The present invention therefore provides a method of cryopreservation sperm employing multilayer insulation and immersion into liquid nitrogen using at least 2 layers, and typically 3-4 layers of thermal insulation.

The invention also provides a container based insulation unit and system for cryopreservation of sperm having a first layer insulation container, such as a commercially available Mini straw, Medium straw, Macro straw, semen bag or other container, such as flat box, blood bag and the like; a second insulation layer of larger size; a third insulation layer of a larger size container (or partial insulation layers). A sperm suspension is first insulated by the first layer container, one or more first layer container(s) are insulated by a second layer container, and one or more second container are insulated by a third layer container. An Insulation unit plus sperm suspension forms a freezing unit, and one or more freezing units may be immersed into liquid nitrogen for controlled freezing.

The invention may further provide a method of controlling cooling rate by providing sperm suspension or other liquid sample, providing a multilayer insulation unit, insulating the sample, immersing it into liquid nitrogen, wherein the sample is cooled at a cooling rate controlled by the insulation unit. The cooling rate R is believed to be described by the formula:

$$R=kA(T1-T2)/mcL$$

wherein k is thermal conductivity (w/m·k), A is the cross section area of the freezing unit; T1 is initial temperature; T2 is final temperature; m is mass of the freezing unit; c is the specific heat; L is thickness of the freezing unit.

To control the cooling rate, the invention controls the elements of the insulation unit, for example, by changing the number of insulation layers. The cooling rate decreases while insulation layer increase. One layer may be too fast, killing some species of sperm. Two layers may be moderately fast, and may be good for some species, such as mice. Three or four layers may control the cooling rate to −10 to −60° C./min., which is ideal for most species.

When the number of insulation layers changes, four (4) parameters (K, m, c, L) will be changed, so it is most effective way to change or control the cooling rate. In each layer one may also change the K—thermal conductivity, A—cross section area, m—mass of the freezing unit (for example, number of straw, sample volume in the straw), c—specific heat, L—thickness, so that the cooling rate will be changed. These five (5) parameters can be changed, one of them or more, and combinations of changes can fine tune the cooling rate.

One may also change the final temperature and thermal conductivity of the cryogen. The preferred cryogen and temperature in the present invention is liquid nitrogen at −196° C. When the same freezing unit is immersed into a lower temperature, for example, −250° C., cooling rate will be faster. When the freezing unit is immersed into less thermal conductivity cryogen, liquid nitrogen vapor at −196° C., cooling rate will be slower. Further, when immersed or buried into dry ice at −79° C., a much slower cooling rate achieved.

Another advantage of the present invention is the first insulation containers which are also used as packaging containers, are insulated and packaged into a second container which are also used as storage container. So the sorting and packaging process is done before cooling and freezing, eliminating the procedure in prior art which carry out this procedure after freezing and must be done in the liquid nitrogen or liquid nitrogen vapor at −196° C.

Also, the invention may provide a method of generating cooling rate gradient by providing at least two different insulation units; providing liquid sham sample or sperm suspension; insulating the sperm suspension in each unit; immersion at least two different unit separately into liquid nitrogen, one unit one time, two different cooling rates produced; immersion at least two different units simultaneously in liquid nitrogen with a suitable rack, keeping suitable space, so that at least two cooling rate are produced. The cooling rate set or cooling rate gradient produced with above two methods, may be same, similar or different, but can repeatable produced once the condition is fixed.

The invention may provide a method of optimizing cooling conditions of sperm by providing a sperm suspension; providing a plurality of different insulation units; insulating the sperm suspension in each unit; immersing them into liquid nitrogen, separately or simultaneously; thawing the samples; evaluating sperm quality; and finding the corresponding unit which gave the best results The present invention therefore provide an improved method and system of freezing sperm and other biological samples which reduces complexity of the materials and processes employed. The method and system of freezing sperm carefully controls cooling rate during the freezing process, and employs improved and easy-to-use containers for the sperm suspension. The present invention also provides a method for determining optimum cooling rate during freezing of sperm which may be readily replicated.

The present invention further provides one or more of the following advantages:

1) The cooling rate is controlled by the thermal features of the insulation layer(s) and can be precisely controlled by physical means.

2) There is direct use liquid nitrogen (not liquid nitrogen vapor, and not −80° C. freezer) for cooling.

3) It can produce a serial cooling rate or cooling rate gradient with one operation, this feature can be used to optimize the current protocol by determining the ideal cooling rate for the specific strain or individual, also can determine the ideal combination of cooling rate and cryoprotectant, will solve the problem that some species (e.g., boar) do not have a good protocol for commercial level use. This minimizes the number of experiments.

4) The sorting and packaging occurs before cooling, avoiding performing this inside the liquid nitrogen after freezing which is harmful for the sample and hazardous to personnel.

5) It consumption less liquid nitrogen, which is expensive.

6) The method allows use of many novel packaging containers which cannot be used with current method. For example, for a small quantity of sperm sample from genetic modified model mice or fish, it can be frozen in very small short straw, PCR tube, glass capillary, to save storage space. This has special significance for transgenic mice and fish, which over 5000 new mouse strains will be created yearly. For large quantity from a boar or horse, it can be frozen in very long tube with a small diameter of 2 to 3 mm and capacity of 5 ml, and the long tube (first insulation layer) can be folded into a flat box (second insulation layer).

7) There is no need for electricity or computer control, and it can operate on site in the field.

8) With the novel method and device, the automation process of sperm cryopreservation will be easier.

9) The double, triple or more layers of insulation (packaging) may also serve as multi barriers to HIV during long term storage, which is a great concern for human sperm storage.

10) For bull boar or horse sperm, the protocol for each individual can be developed to solve the difference between male-to-male, taking advantage of the genetic merit to the maximum extent.

11) The devices may be made of plastic at low cost.

12) The traditional pathway of sperm cryopreservation (sample collection, followed by sample processing, followed by packaging, followed by freezing in liquid nitrogen vapour and sorting, followed by storage, followed by utilization) will be changed and simplified to: sample collection, followed by sample processing, followed by first layer insulating (packaging) sorting, followed by second layer insulating (packaging), followed by third or more layer insulating (packaging), followed by cooling and freezing in liquid nitrogen, followed by storage, followed by utilization.

13) The concept of serial cooling rate or cooling rate gradient can be used both in the process of freezing and before freezing.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of cryopreservation of sperm comprising:
   providing a liquid suspension of sperm to be frozen;
   placing the liquid suspension of sperm into a plurality of first containers comprising plastic straws having walls of a thickness and thermal conductivity;
   placing the plurality of plastic straws into a second insulating container having thermally insulating walls of a thickness and thermal conductivity, the plastic straws being arranged within the second insulating container in a pair of adjacent, straight rows of a plurality of plastic straws, with each of plastic straws being adjacent to the second insulating container;
   placing the second insulating container containing the pair of rows of a plurality of plastic straws into a third insulating container, the third insulating container having thermally insulating walls of a thickness and thermal conductivity;
   providing a liquid cryogenic fluid;
   plunging the third insulating container with the second insulating container and pair of rows of a plurality of plastic straws containing liquid suspension of sperm from an initial temperature in a range of about 5° C. to room temperature directly into the liquid cryogenic fluid, the tops of the plastic straws being below a surface thereof after immersion; and freezing the sperm as a result of having been plunged directly into the liquid cryogenic fluid, without adding an amount of cryoprotectant sufficient to achieve vitrification, at a cooling rate of from about −10 and about −100° C. per minute sufficient to maintain post-thaw quality of the sperm, the cooling rate being controlled solely by the thermal conductivity of the walls of the plastic straws, the walls of the second and third insulating containers and any substance between the walls of the plastic straws and the second and third insulating containers, and wherein the cooling rates of the liquid suspension of sperm in the plastic straws are comparable to each other during freezing of the sperm.

2. The method of claim 1 wherein the second or third insulating container includes a thermally insulating pocket adjacent to the ends of the pair of rows of plastic straws.

3. The method of claim 1 wherein the cooling rate of the sperm is controlled to be between about −10 and about −60° C. per minute.

4. The method of claim 1 further including storing the frozen sperm in the plurality of first containers without transferring the frozen sperm into another container following the freezing process.

5. The method of claim 1 wherein the second insulating container comprises a plastic box.

6. The method of claim 1 wherein the third insulating container comprises a plastic bag or other flexible packaging.

7. The method of claim 1 further including one or more additional flexible insulating containers over the third insulating container.

8. The method of claim 1 wherein the third insulating container comprises a plastic bag, and further including sealing an end of the bag and immersing the plastic bag into the liquid cryogenic fluid.

9. The method of claim 1 further including storing the frozen sperm in the plastic straws without transferring the frozen sperm into another container following the freezing process.

10. The method of claim 1 wherein the liquid cryogenic fluid is liquid nitrogen.

11. A method of cryopreservation of sperm comprising:
providing a liquid suspension of sperm to be frozen;
placing the liquid suspension of sperm into a plurality of first containers comprising plastic straws having walls of a thickness and thermal conductivity;
placing the plurality of plastic straws into a second insulating container comprising a plastic box having thermally insulating walls of a thickness and thermal conductivity, the plastic straws being arranged within the plastic box in a pair of adjacent, straight rows of a plurality of plastic straws, with each of plastic straws being adjacent to the walls of the plastic box;
placing the second insulating container containing the pair of rows of a plurality of plastic straws into a third insulating container comprising a plastic bag, the plastic bag having thermally insulating walls of a thickness and thermal conductivity;
providing a liquid cryogenic fluid;
plunging the plastic bag with the plastic box and pair of rows of a plurality of plastic straws containing liquid suspension of sperm from an initial temperature in a range of about 5° C. to room temperature directly into the liquid cryogenic fluid, the tops of the plastic straws being below a surface thereof after immersion; and
freezing the sperm as a result of having been plunged directly into the liquid cryogenic fluid, without adding an amount of cryoprotectant sufficient to achieve vitrification, at a cooling rate of from about −10 and about −100° C. per minute sufficient to maintain post-thaw quality of the sperm, the cooling rate being controlled solely by the thermal conductivity of the walls of the plastic straws, the walls of the plastic box and plastic bag and any substance between the walls of the plastic straws and the plastic box and plastic bag, and wherein the cooling rate of the liquid suspension of sperm in the plastic straws are comparable to each other during freezing of the sperm.

12. The method of claim 11 wherein the plastic box or plastic bag includes a thermally insulating pocket adjacent to the ends of the pair of rows of plastic straws.

13. The method of claim 11 wherein the cooling rate of the sperm is controlled to be between about −10 and about −60° C. per minute.

14. The method of claim 11 further including storing the frozen sperm in the plastic straws and within the plastic box without transferring the first containers containing frozen sperm into another container following the freezing process.

15. The method of claim 11 further including one or more additional plastic bags over the plastic bag.

16. The method of claim 11 further including sealing an end of the bag and immersing the plastic bag into the liquid cryogenic fluid.

17. The method of claim 11 wherein the liquid cryogenic fluid is liquid nitrogen.

* * * * *